United States Patent
Ogata et al.

Patent Number: 5,556,614
Date of Patent: Sep. 17, 1996

[54] DEODORANT COMPOSITION

[75] Inventors: Kazumi Ogata, Toyonaka; Osamu Kawahira, Sakai, both of Japan

[73] Assignee: Senju Pharmaceutical Co., Ltd., Osaka, Japan

[21] Appl. No.: 323,618

[22] Filed: Oct. 17, 1994

[30] Foreign Application Priority Data

Oct. 22, 1993 [JP] Japan .................. 5-264438

[51] Int. Cl.$^6$ .................. A61K 7/32; A61K 31/66
[52] U.S. Cl. .................. 424/65; 424/47; 424/76.2; 514/75; 514/90; 514/91; 514/458
[58] Field of Search .................. 424/565, 76.1, 424/47, 76.2; 514/458, 75, 90, 91

[56] References Cited

U.S. PATENT DOCUMENTS

| | | | |
|---|---|---|---|
| 4,564,686 | 1/1986 | Ogata | 549/220 |
| 4,914,197 | 4/1990 | Yamamoto et al. | 536/117 |

*Primary Examiner*—Shelley A. Dodson
*Attorney, Agent, or Firm*—Wenderoth, Lind & Ponack

[57] ABSTRACT

This invention provides a deodorant composition comprising a phosphoric diester compound of the following formula or a pharmacologically acceptable salt thereof as an active deodorant ingredient.

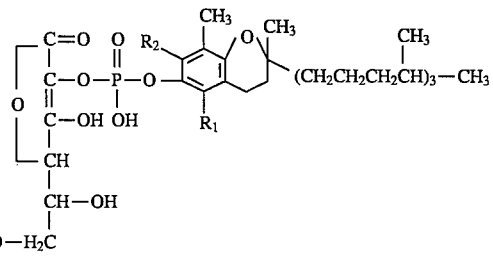

(wherein $R_1$ and $R_2$ are the same or different and each represents a hydrogen atom or a methyl group).

The deodorant composition of this invention has a potent deodorizing action and yet does not stimulate the mucosa of the eye, nose and throat. Therefore, it can be used in various industrial and household applications.

1 Claim, No Drawings

DEODORANT COMPOSITION

BACKGROUND OF INVENTION

1. Field of the Invention

This invention relates to a useful deodorant composition. More particularly, this invention relates to a deodorant composition comprising an ascorbyl tocopheryl phosphate compound or a pharmacologically acceptable salt thereof.

2. Description of the Prior Art

A diversity of deodorants including active charcoal and glyoxal are available on the market. Meanwhile, it is known that more than hundreds of substances can be sources of malodors and these substances are roughly classified into nitrogen compounds such as ammonia and amines and sulfur compounds such as hydrogen sulfide and mercaptans.

The performance rating of a deodorant is made according to how many sources of malodor it may deal with and how quickly it does so. In addition to these criteria, how conveniently it can be used is another important criterion.

However, there has not been developed a deodorant that fully meets with these criteria. Therefore, research and development work is in progress for finding better deodorants.

Under the circumstances the inventors of this invention did much research to create a satisfactory deodorant. As a consequence, the inventors discovered that the active ingredient compound of the deodorant composition of this invention has an outstanding deodorizing action and, based on this finding, did further research and perfected this invention.

SUMMARY OF THE INVENTION

This invention is, therefore, directed to a deodorant composition comprising a phosphoric diester compound of the following formula (hereinafter referred to as the present compound) or a pharmacologically acceptable salt thereof as an active deodorant ingredient.

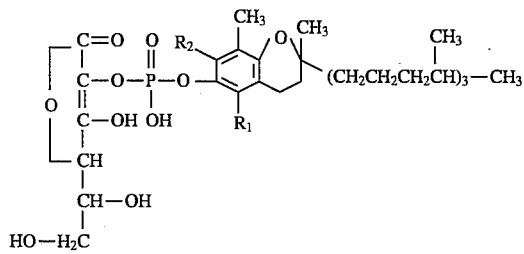

(wherein $R_1$ and $R_2$ are the same or different and each represents a hydrogen atom or a methyl group).

DETAILED DESCRIPTION OF THE INVENTION

The present compound, which is incorporated in the deodorant composition of this invention, is a phosphoric diester compound which, as can be seen from the above chemical formula, consists of an ascorbic acid unit and a tocopherol unit as linked together by a phosphoric acid unit.

The present compound for use in the deodorant composition of this invention can be synthesized by the processes described in JP Publication H-2-44478 and JP Kokai S-62-205091, among others, or any processes analogous thereto. For this compound, a variety of uses such as an anticataract agent, a prophylactic and therapeutic agent for climacteric disturbance, a skin care cosmetic (JP Publication H-2-44478), etc. are already known.

However, it has not been reported that the present compound has a potent deodorizing action.

The present compound for use in the deodorant composition of this invention may be whichever of the free compound and its pharmacologically acceptable salt. While the salt typically includes salts with alkali metals such as sodium, potassium, etc. and salts with alkaline earth metals such as calcium, magnesium, etc., other pharmacologically acceptable salts can also be employed where appropriate.

Depending on the objective and need, one or more species of the present compound and its pharmacologically acceptable salt can be incorporated in the deodorant composition of this invention.

The deodorant composition of this invention can be formulated into liquid, solid, gel and other preparations by the per se known procedures and be used in various industrial and household applications. The liquid deodorant preparation may for example be a solution in water or a suitable organic solvent such as ethanol, an emulsion as formulated with a suitable surfactant, or an aerosol prepared by filling an atomizer or the like with such a liquid composition and a propellant. The solid deodorant preparation may for example be a powder or dust prepared by admixture with a finely divided inorganic material such as silica or perlite, a product manufactured by impregnating a paper or other porous matrix with the formulation, or a product manufactured by compounding the formulation with a synthetic resin such as polyethylene. The deodorant gel may for example be a product manufactured by incorporating the formulation into a natural or synthetic polymer gel base such as agar, carrageenan or polyethylene glycol. If required, a surfactant, germicide, perfume and/or color may be incorporated in suitable amounts in such preparations.

In household applications, the deodorant composition of this invention can be used for the elimination of malodors from the room, refrigerator, washroom and dust bin as well as for the removal and masking of the body odor. In industrial applications, this deodorant can be applied to the removal of fetid odors from a sewage plant, fish processing plant, fishmeal manufacturing plant, animal quarters, animal feces/poultry droppings drying plant, pulp plant and so forth.

For application of the deodorant composition of this invention, the concentration of the present compound should be selected according to the species of compound used, intensity of the malodor, and source of the malodor, among other factors. The generally recommended concentration in the space to be deodorized is not less than about 0.01% by weight and that in the open environment is not less than about 0.1% by weight.

Unless contrary to the object of this invention, the deodorant composition of this invention can be further formulated with various ingredients which are commonly incorporated in industrial and household deodorants, for example adsorbents such as activated carbon, silica gel, alumina and so on.

EXAMPLE

The following experimental examples and working examples are intended to describe this invention in further detail.

Experimental Example 1

Deodorant Effect of the Present Compound on the Odor of Raw Sardine

Maiwashi (spotlined sardine, *Sardinops melanostictus*) were eviscerated and the deodorizing effect of the present compound on the characteristic offensive odor of sardine on the hands was evaluated.

Test Material

The spray according to Example 1, which appears hereafter, was used.

Method

After an eviscerator had completed evisceration of 35 sardine, he washed both hands with tap water and wiped clean with a towel. Then, 5 panelists including the eviscerator confirmed that washing with tap water had not removed the fish odor on the hands completely.

Then, with the left hand being left untreated, the right hand was evenly sprayed with the deodorant compostion of this invention. About 5 minutes after spraying, when the right hand had dried, the odor of the right hand was evaluated by the five panelists according to the following scoring criteria.

| Scoring criteria | |
|---|---|
| • Fish odor was completely removed | 5 points |
| • Though a faint odor remained, it was not easy to decide whether it is a fish odor. | 4 points |
| • Though a slight fish odor remained, it was not so offensive | 3 points |
| • There was a fish odor but a deodorizing effect was apparent | 2 points |
| • Fish odor was slightly removed but the residual odor was still unpleasing | 1 points |
| • Compared with the left hand, no deodorizing effect was found | 0 points |

Results

The results are shown in Table 1.

TABLE 1

| Panelist | A | B | C | D | E |
|---|---|---|---|---|---|
| Score | 4 | 4 | 3 | 4 | 3 |

It is clear from Table 1 that the present compound has a potent deodorizing action.

Experimental Example 2

Deodorant Effect of the Present Compound on the Odor of Athletic Shoes

The deodorant effect of the present compound on the odor of athletic shoes was evaluated.

Test Material

The spray according to Example 1 given hereafter was used.

Method

Using a pair of athletic shoes worn intermittently for one month after purchase, the deodorant effect of the present compound on the characteristic shoe odor due to perspiration of the feet was evaluated.

With the left shoe being used as untreated control, the right shoe was sprayed with the deodorant of this invention. The immediate deodorizing effect after spraying and the deodorizing effect on the odor after about 5 hours of continuous wear following application of the spray were evaluated by 5 panelists according to the same scoring criteria as used in Experimental Example 1.

Results

The results are shown in Table 2.

TABLE 2

| Panelist | A | B | C | D | E |
|---|---|---|---|---|---|
| Immediately after spraying | 4 | 5 | 5 | 4 | 3 |
| After 5 hr of continuous wear | 3 | 3 | 4 | 3 | 2 |

It is clear from Table 2 that the present compound has a potent deodorizing action.

Experimental Example 3

Deodorant Effect of the Present Compound on the Odor of Maiwashi Viscera

The deodorant effect of the present compound on the odor of the viscera of sardine was evaluated.

Test material

The spray according to Example 1 given hereafter was used.

Method

Two clear PVC bags were provided and one of them was filled with about 30 g of sardine viscera. The other bag was filled with the same amount of sardine viscera and, then, evenly sprayed with the deodorant composition of this invention. The bags were allowed to remain unsealed in a room for 24 hours and compared for visceral odor.

Results

The untreated sardine viscera had emanated an intense rancid odor but the sardine viscera treated with the deodorant composition of this invention had remained almost odorless even without a hint of the visceral odor characteristic of sardine.

Example 1

Spray

In a 30% aqueous solution of ethanol is dissolved L-ascorbyl DL-tocopheryl phosphate potassium (EPC-K) at 1.0% concentration and this solution is adjusted to pH 6.5 and filled in a commercial sprayer.

Example 2

Gel

| | |
|---|---|
| EPC-K | 0.1 g |
| Ethanol | 30 ml |
| Carboxyvinyl polymer | 1.0 g |
| Triethanolamine | q.s. |

| | |
|---|---|
| Sterilized pure water to make | 100 ml |
| pH | 7.5 |

Using the above ingredients, a gel preparation is manufactured in the conventional manner.

The deodorant composition of this invention has a potent deodorizing action and yet does not stimulate the mucosa of the eye, nose and throat. Therefore, it can be used in various industrial and household applications.

What is claimed is:

1. A method for deodorizing malodors which comprises contacting a source of the malodors with a deodorizing effective amount of a phosphoric diester compound of the formula

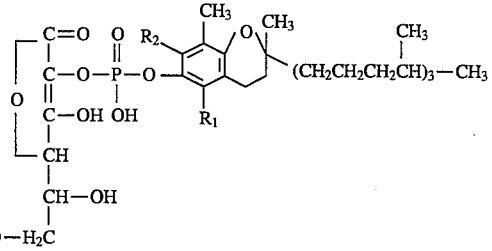

wherein $R_1$ and $R_2$ are the same or different and each represents a hydrogen atom or a methyl group or a pharmacologically acceptable salt thereof.

* * * * *